(12) United States Patent
Hoppe et al.

(10) Patent No.: US 8,107,708 B2
(45) Date of Patent: Jan. 31, 2012

(54) METHOD FOR CORRECTING TRUNCATION ARTIFACTS

(75) Inventors: Stefan Hoppe, Amberg (DE); Joachim Hornegger, Effeltrich (DE); Günter Lauritsch, Erlangen (DE)

(73) Assignee: Siemens Aktiengesellschaft (DE)

( * ) Notice: Subject to any disclaimer, the term of this patent is extended or adjusted under 35 U.S.C. 154(b) by 875 days.

(21) Appl. No.: 12/217,650

(22) Filed: Jul. 8, 2008

(65) Prior Publication Data

US 2009/0016592 A1 Jan. 15, 2009

(30) Foreign Application Priority Data

Jul. 9, 2007 (DE) .......................... 10 2007 032 082

(51) Int. Cl.
*G06K 9/00* (2006.01)
(52) U.S. Cl. .......................................... 382/131; 378/19
(58) Field of Classification Search .................. 382/128, 382/131, 132; 378/4, 19, 901
See application file for complete search history.

(56) References Cited

U.S. PATENT DOCUMENTS

| | | | |
|---|---|---|---|
| 5,640,436 A | 6/1997 | Kawai et al. | |
| 6,856,666 B2 | 2/2005 | Lonn et al. | |
| 2006/0120507 A1 | 6/2006 | Brunner et al. | |
| 2011/0096968 A1* | 4/2011 | Deykoon | 382/131 |

FOREIGN PATENT DOCUMENTS

| | | |
|---|---|---|
| DE | 103 45 704 A1 | 8/2004 |
| DE | 10 2006 014 629 A1 | 10/2007 |

OTHER PUBLICATIONS

Feldkamp et al.; "Practical Cone-Beam Algorithm". J. Optical Society of America; Jun. 1984; pp. 612-619; vol. 1, No. 6.
Pack et al.; "Investigation of saddle trajectories for cardiac CT imaging in once-beam geometry"; Institute of Physics Publishing; 2004; pp. 2317-2336; Phys. Med. Biol. 49.
Alexander Katsevich; "Image reconstruction for the circle-and-arc trajectory"; Institute of Physics Publishing, Physics in Medicine and Biology; 2005; pp. 5059-5072; Phys. Med. Biol. 49.
Alexander Katsevich; "Image reconstruction for the circle-and-arc line trajectory"; Institute of Physics Publishing, Physics in Medicine and Biology; 2005; pp. 3349-2265; Phys. Med. Biol. 50.
Nett et al.; "A Cone-beam FBP reconstruction algorithm for short-scan and super-short-scan source trajectories"; In Fully 3D Reconstruction in Radiology and Nuclear Medicine; Jul. 6-9, 2005; pp. 1-9; Salt Lake City UT, USA.

(Continued)

*Primary Examiner* — Jurie Yun

(57) ABSTRACT

The invention relates to a method for correcting truncation artifacts in a reconstruction method for computed tomography recordings. The projection images are recorded by an x-ray image detector being extended by determining the attenuation of the radiation outside the projection image for pixels. Non-horizontal filter lines are extended by transaxial and axial artificial extension of the x-ray image detector for the purposes of truncation correction. The truncation correction for non-horizontal filter lines being carried out according to a method from at least one of the following groups: truncation correction takes place regardless of the specific location and orientation of the filter lines; truncation correction takes place as a function of the specific position and orientation of the filter lines, with the filter lines themselves being retained; and truncation correction takes place by introducing new modified filter lines, with filtering taking place along offset artificially extended filter lines.

13 Claims, 10 Drawing Sheets

OTHER PUBLICATIONS

Pack et al.: "Cone-beam reconstruction using 1D filtering along the projection of M-lines"; Institute of Physics Publishing; 2005; Inverse Problems 21; pp. 1105-1120.

Hsieh et al.; "A novel reconstruction algorithm to extend the CT scan field of view"; Am. Assoc. Phys. Med.; Sep. 2004; Medical Physics vol. 31, No. 9; pp. 2385-2391.

Zellerhoff et al.; "Low contrast 3D-reconstruction from C-arm data"; SPIE Medical Imaging; 2005; 5745; pp. 1605-7422.

Flohr et al.; "Image reconstruction and imager quality evaluation for a 16-slice CT scanner"; Medical Physics 30 (5); May 2003; pp. 832-845.

Kacheirieβ et al.; "Extended parallel back projection for standard three-dimensional and phase correlated four-dimensional axial and spiral cone-beam CT with arbitrary pitch, arbitrary cone-angle, and 100% does usage"; Medical Physics 31 (6); Jun. 2004; pp. 1623-1641.

Magnusson et al.; "Handling of Long Objects in Iterative Improvement of Nonexact Reconstruction in Helical Cone-Beam CT"; IEEE transactions on medical imaging; vol. 25, No. 7; Jul. 2006; pp. 935-940.

S. Hoppe, J. Hornegger, G. Lauritsch, F. Dennerlein and F. Noo; "Truncation Correction for Non-horizontal Filter Lines", 9th International Meeting on Fully Three-Dimensional Image, Reconstruction in Radiology and Nuclear Medicine, Jul. 9-13, 2007, Lindau, Germany (submitted).

* cited by examiner

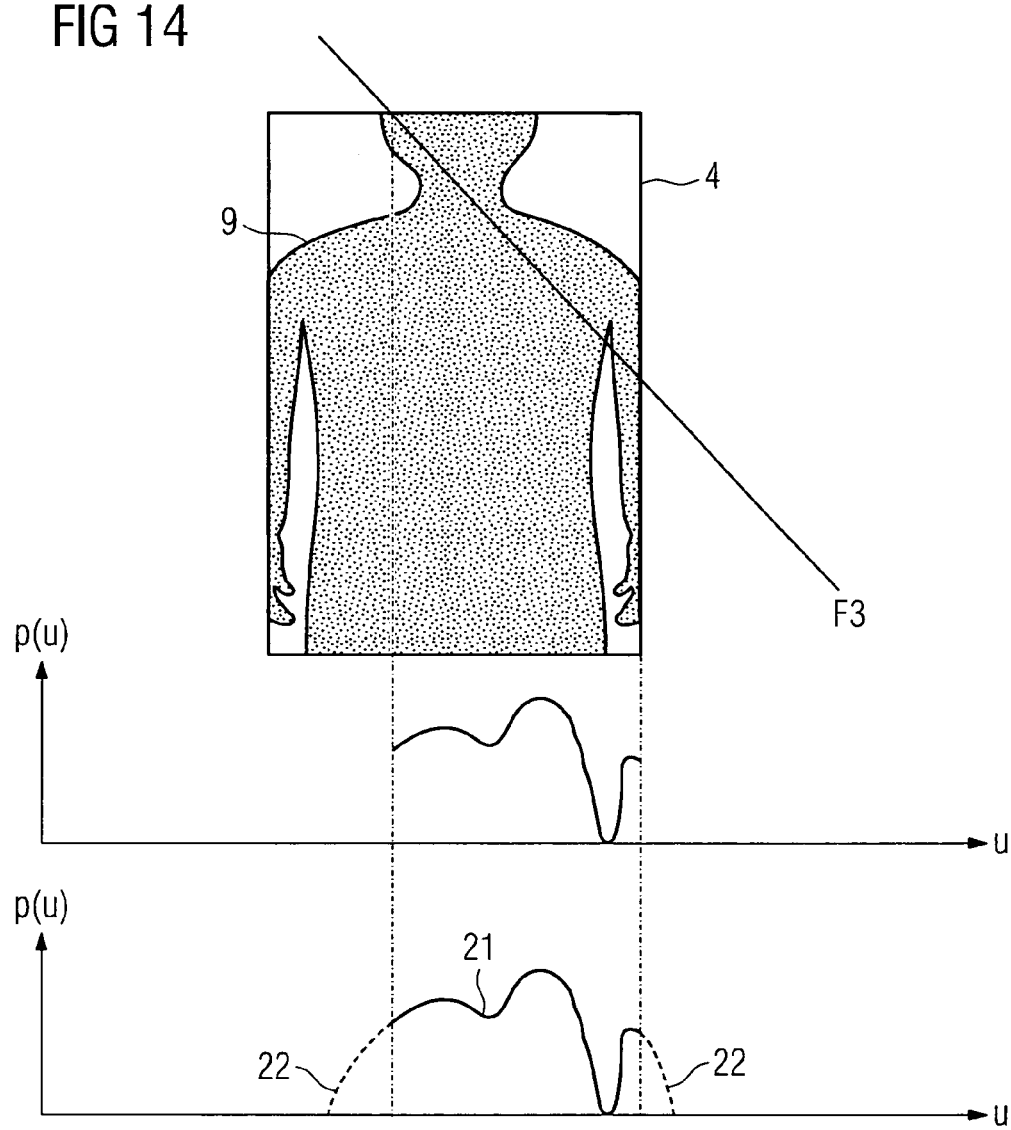

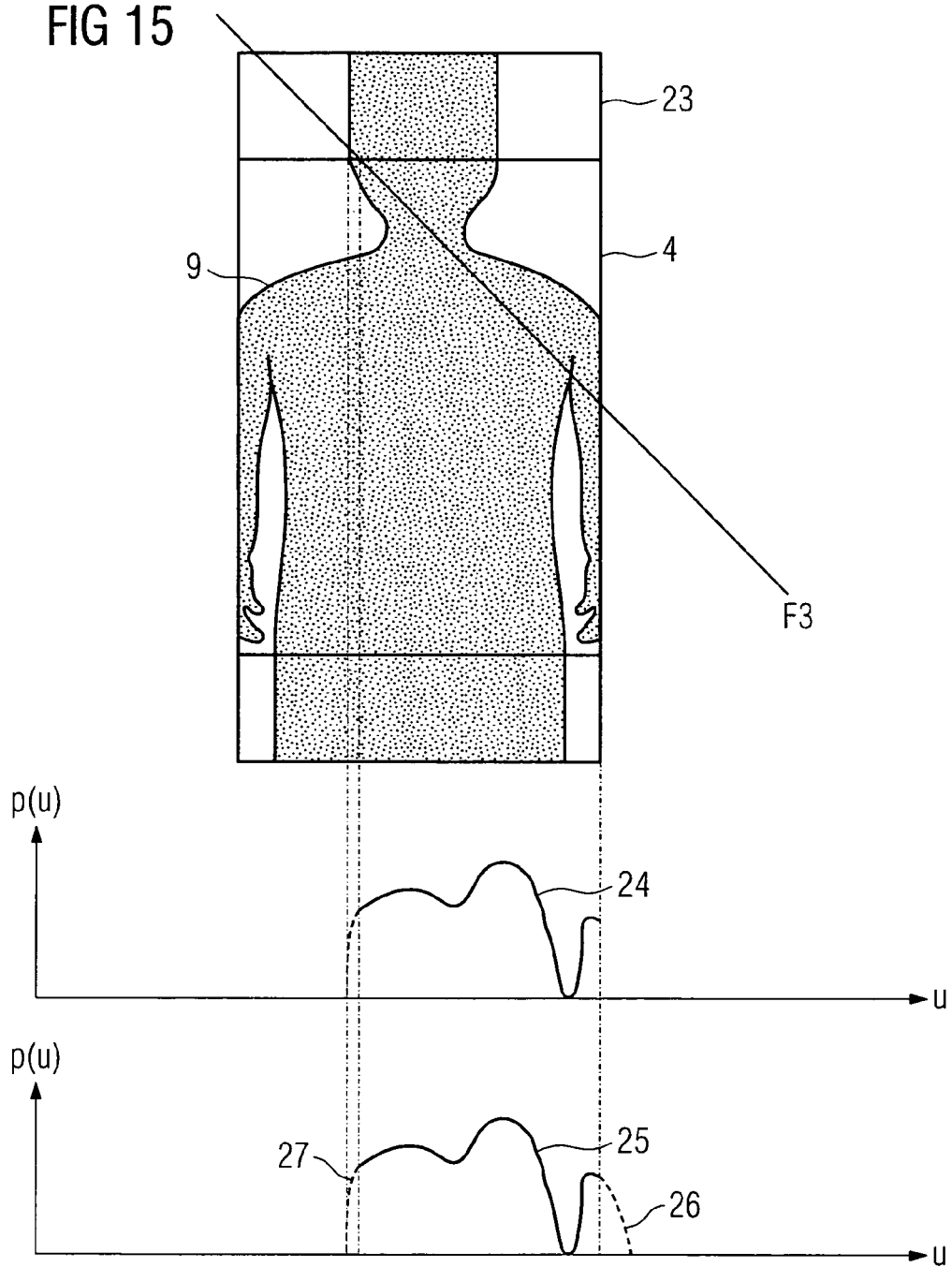

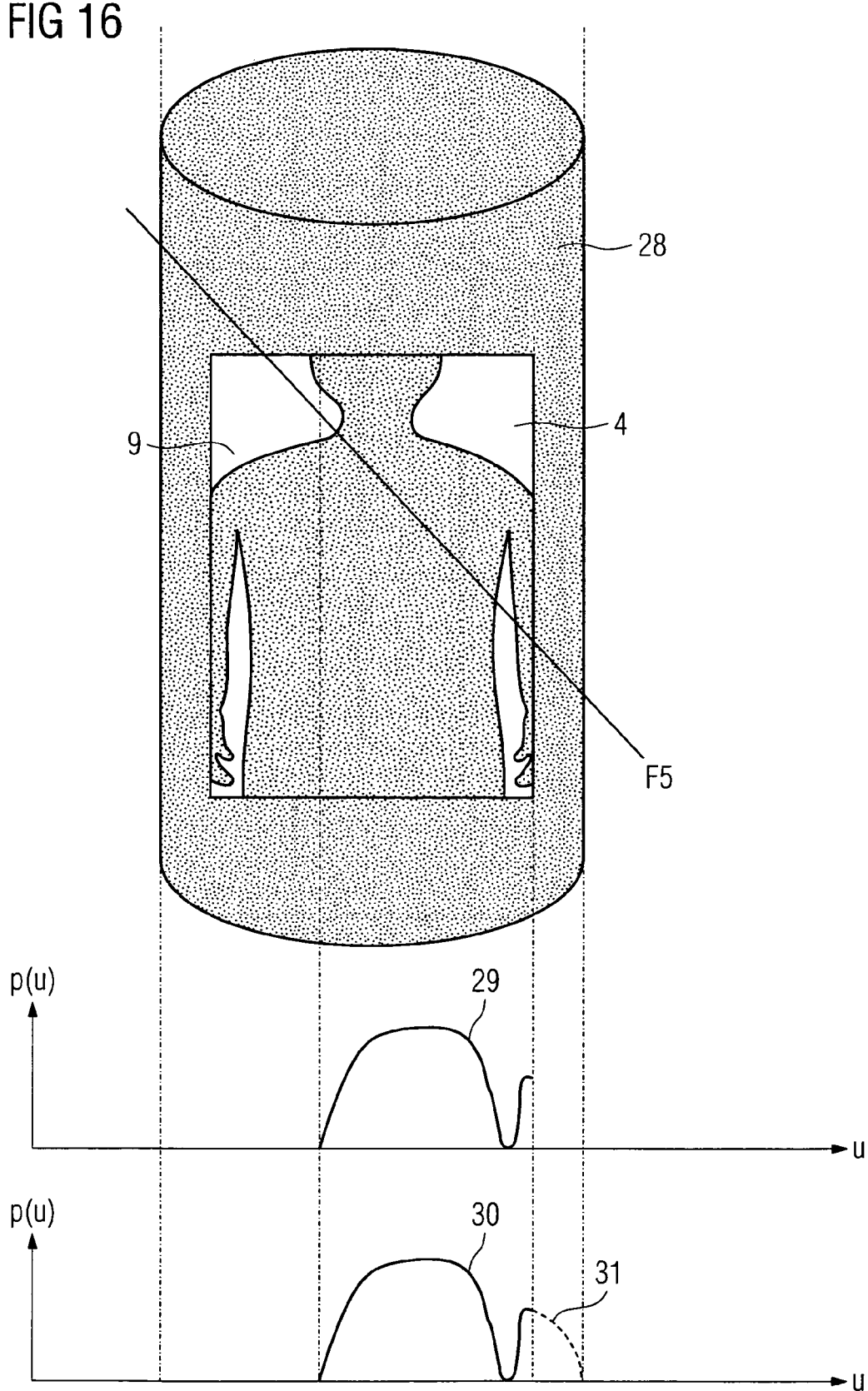

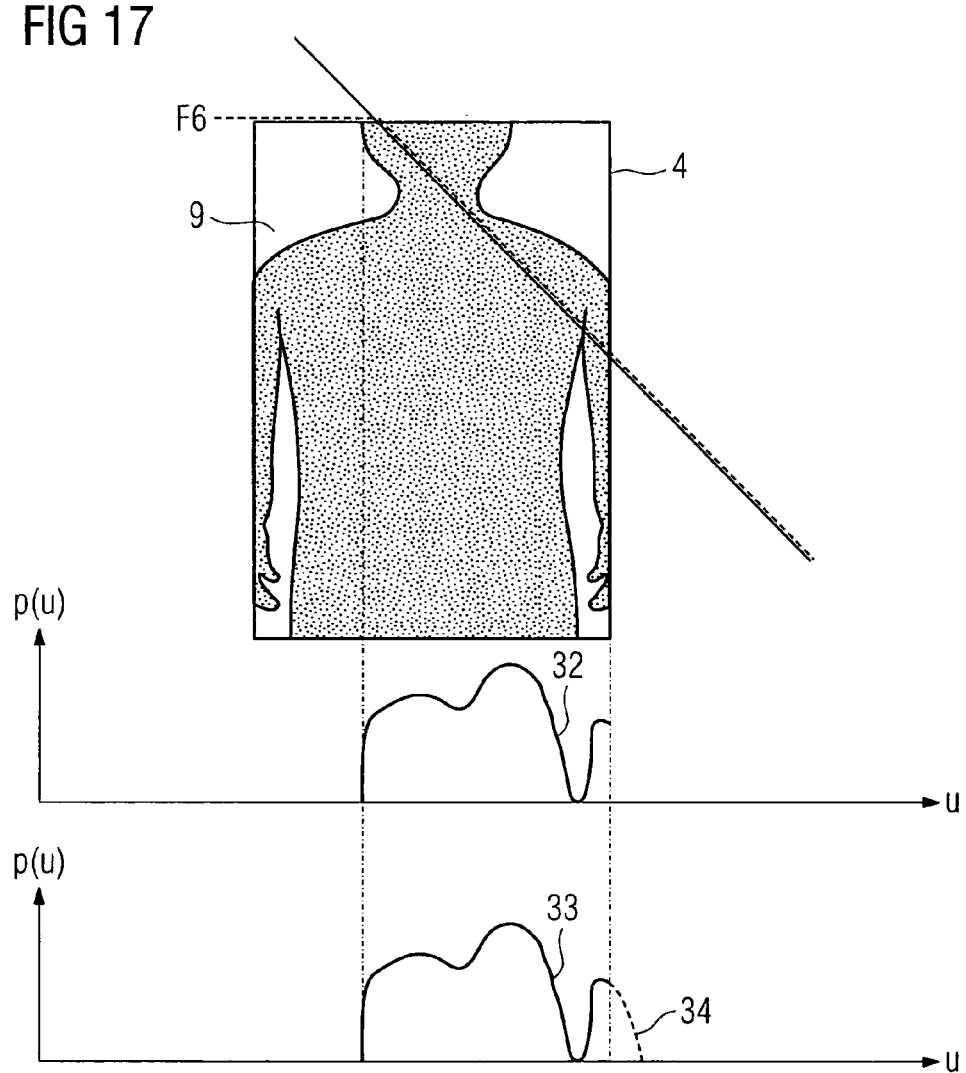

METHOD FOR CORRECTING TRUNCATION ARTIFACTS

CROSS REFERENCE TO RELATED APPLICATIONS

This application claims priority of German application No. 10 2007 032 082.7 filed Jul. 9, 2007, which is incorporated by reference herein in its entirety.

FIELD OF THE INVENTION

The invention relates to a method for correcting truncation artifacts in a reconstruction method for computed tomography recordings.

BACKGROUND OF THE INVENTION

Such a correction method for truncation artifacts can be deployed with an x-ray diagnostic facility for angiography as known from US 2006/0120507 A1, which is shown by way of example in FIG. 1. The x-ray diagnostic facility has a C-arm 2 supported in a rotatable manner on a stand 1, at the end of which C-arm 2 an x-ray radiation source, for example an x-ray emitter 3, and an x-ray image detector 4 are positioned.

The x-ray image detector 4 can be a rectangular or square, flat semiconductor detector, which is preferably made of amorphous silicon (aSi).

In the beam path of the x-ray radiation source 3 is a patient support table 5 for recording for example the heart of a patient to be examined. Connected to the x-ray diagnostic facility is an image system 6, which receives and processes the image signals from the x-ray image detector 4. The x-ray images can then be viewed on a monitor 7.

The movable components 2 to 5 can also be supported individually or in a common manner on robot arms.

To create 3D data sets the C-arm 2, which is supported in a rotatable manner, is rotated with the x-ray emitter 3 and x-ray image detector 4 in such a manner that, as shown schematically in the top view of the axis of rotation in FIG. 2, the x-ray radiation source 3 moves on one circumferential path 7 and the x-ray image detector 4 moves on one circumferential path 8 around an examination object 9. The circumferential paths 7 and 8 can be traveled wholly or partially to create a 3D data set.

The examination object 9 can be for example an animal or human body or even a phantom body.

The x-ray radiation source 3 emits an x-ray beam bundle 6, which leaves a beam focus of the x-ray radiation source 3 and strikes the x-ray image detector 4.

The x-ray radiation source 2 and the x-ray image detector 4 move respectively around the examination object 9 in such a manner that the x-ray radiation source 2 and the x-ray image detector 4 are located facing each other on opposite sides of the examination object 9.

A significant processing step for the 3D reconstruction by means of filtered backprojection (FBP) is the filtering of the projection data along predefined lines in the x-ray image detector. The non-local nature of the filter core, for example the ramp filter or Hilbert filter, means that the filter lines have to run through the entire projection of the examination region and cannot be cut off, even if only part of the body region, for example the so-called region of interest (ROI), is to be reconstructed. The limited detector width however results in cut off projections of the examination region in many recordings, in particular when using the above-mentioned C-arm system, as this cannot be covered completely by the field of view (FoV). This results in cut-off filter lines in these projections. This produces pronounced reconstruction artifacts, which falsify the result and hinder, complicate or render impossible its qualified diagnosis. One example of this is an examination of the abdomen or thorax. A distinction can be made between two types of truncation:
(1) transaxial truncation and
(2) axial truncation.

Transaxial truncation is produced by examination objects that are cut off along the horizontal detector axis.

Axial truncation is produced by examination objects that are cut off along the vertical detector axis. Therefore in the case of the Feldkamp algorithm described in [1], with which filtering operates along horizontal lines in the x-ray image detector, only transaxial truncation of the filter lines is possible. However the development of new approximative and exact reconstruction algorithms and the use of novel scanning paths, such as circle and line, circle and arc, saddle, means that non-horizontal filter lines have also been introduced, as described for example in Pack et al. [2] and [6], Katsevich [3] and [4] as well as Nett et al. [5]. This means that both transaxial truncation and axial truncation can occur (see also FIG. 3). Such algorithms therefore require a new method, which is able to correct both types of truncation effectively. Since the algorithms promise a very high image quality, the solution to the truncation problem would be an important and central contribution to the resolution of reconstruction problems in computed tomography.

FIG. 3 shows possible truncations for non-horizontal filter lines by way of example. The contours of the examination object are mapped on the x-ray image detector 4. One filter line F1 is cut off transaxially on both sides. One filter line F2 is cut off axially on both sides. One filter line F3 is cut off axially on the left and transaxially on the right. One filter line F4 has no truncation. Truncation always occurs when a filter line exits from the x-ray image detector 4 before it exits from the examination object 9. Significant reconstruction artifacts result for every point on a truncated filter line. This can be the case for the majority of points in the case of non-horizontal filter lines.

In the case of C-arm systems, until now 3D reconstruction was carried out using the Feldkamp algorithm, which manages with a planar, circular scanning path. It uses only horizontal filter lines, so that only transaxial filter line truncation can occur. A hybrid solution has proven very effective for correcting transaxial truncation. Hybrid correction is made up of the so-called water cylinder correction and a Gaussian extrapolation, as described by way of example in Hsieh et al. [7], Zellerhoff et al. [8] or Scholz [9]. The method is implemented row by row. It is first checked in each instance using a threshold value whether truncation is present. If so, either water cylinder correction or Gaussian extrapolation is used, depending on the gradient of the (truncated) projection profile at the edge of the detector row in question (see FIG. 4). If the gradient at the left detector edge is positive or the gradient at the right detector edge is negative, water cylinder correction is deployed (see FIG. 5). With water cylinder correction it is assumed that the examination object can be approximated very closely by a water cylinder. To this end the center point and radius of the water cylinder are first determined. The missing projection values are then generated artificially by computer-simulated x-ray beams, which pass through the water cylinder. The detector row is continued with the projection values thus generated. If the gradient at the left detector edge 35 is negative or the gradient at the right detector edge 36 is positive, Gaussian extrapolation is deployed (see FIG. 6). With Gaussian extrapolation the missing projection values are approximated by a Gaussian curve. This produces the absent projection values, as with water cylinder correction.

A Feldkamp based reconstruction algorithm is also used with CT systems. However filtering takes place along non-horizontal lines in the x-ray image detector 4, with the gradients of the filter lines having very low values. With CT systems transaxial truncation cannot take place due to the size of the detector. Therefore only axial truncation has to be dealt with. To this end the x-ray image detector 4 is constantly continued in the axial direction, by repeatedly copying and adding the first and/or last detector row (see FIG. 7) as for example with Flohr et al. [10] or Kachelrieβ et al. [11].

FIG. 4 shows a projection profile p(u) along a cut off detector row. Either water cylinder correction (a) or Gaussian extrapolation (b) is used depending on the gradient of the measured projection values 11 at the edge of the row.

FIG. 5 shows an example of a water cylinder correction for the right detector edge 36. The missing projection values are generated by computer-simulated x-ray beams by means of a water cylinder 12 and used as artificially generated projection values 13 to continue the profile.

FIG. 6 shows an example of Gaussian extrapolation for the right detector edge 36. The missing projection values are approximated by a Gaussian curve 14 and used as artificially generated projection values 15 to continue the profile.

With CT systems truncation correction is carried out by constant axial continuation 16 of the x-ray image detector 4 in the axial direction, as shown in FIG. 7. The sizes of the extension regions are selected here in such a manner that no further filter lines are cut off.

[12] and DE 103 45 704 A1 and U.S. Pat. No. 5,640,436 do not describe any truncation corrections in the axial direction. Roughly speaking the patient can be seen as a cylinder of almost infinite length. With truncation in the transaxial direction a part close to the edge of the object is missing. Corrections try to estimate the edge of the object and to extrapolate the data. This truncation correction is well known in the literature.

With truncation in the axial direction the majority of the object is essentially missing. Close object edges are not present, being estimated and extrapolated. Such extrapolation methods for correcting axial truncation are not known.

DE 103 45 704 A1 and U.S. Pat. No. 5,640,436 deal only with transaxial truncation.

[12] describes the "long object problem", in other words axial truncation, where iterative methods are examined. Axial truncation is therefore not corrected by data extrapolation but by appropriate selection of data in the reprojection and correction of the intermediate result. Section 2.D deals with an extrapolation method, which supplements missing data (see FIG. 5, mask 1). The missing data at the start and end of the scanning path is the result of data sorting from fan-beam to parallel-beam geometry regardless of the shape of the object and the size of the detector. The resulting truncation problem is however equivalent to transaxial truncation and is corrected accordingly.

SUMMARY OF THE INVENTION

The invention is based on the object of configuring a correction method for truncation artifacts of the type mentioned in the introduction, such that truncation correction can also be carried out even with filter lines of any orientation.

The method corrects truncation artifacts in a reconstruction method for computed tomography recordings with truncated projection data in the reconstructed computed tomography images, wherein a radiation source emits divergent radiation, an object to be examined is transilluminated in different projection directions with said divergent radiation, the radiation penetrating the object to be examined is detected by an x-ray image detector and a filtered backprojection is carried out filtering the projection data along predefined non-horizontal lines in the x-ray image detector, with projection images recorded by the x-ray image detector being extended by determining the attenuation of the radiation outside the projection image for pixels.

According to the invention the object is achieved in that for the purposes of truncation correction non-horizontal filter lines are extended by a transaxial and axial artificial extension of the x-ray image detector, with the truncation correction for non-horizontal filter lines being carried out according to a method from at least one of the following groups:

I) Truncation correction takes place regardless of the specific location and orientation of the filter lines.

II) Truncation correction takes place as a function of the specific position and orientation of the filter lines, with the filter lines themselves being retained.

III) Truncation correction takes place by introducing new modified filter lines, with filtering taking place along offset artificially extended filter lines.

According to the invention the truncation correction methods for non-horizontal filter lines are divided into three groups. The methods in group I carry out the correction regardless of the specific position and orientation of the filter lines. They can therefore be applied regardless of the reconstruction algorithm used. The methods in group II carry out the correction as a function of the specific position and orientation of the filter lines. The filter lines themselves are retained. With the method in group III new filter lines are introduced during the course of truncation correction.

The x-ray image detector according to group I) can advantageously be artificially extended transaxially and axially, with the extensions being based on hybrid correction or the transaxial extension being based on hybrid correction and it being possible for the axial extension to take place by means of constant continuation of the x-ray image detector in the axial direction by repeatedly copying and adding the first and last detector rows.

It has proven advantageous, if the filter lines according to group II) are extended artificially, by carrying out a hybrid correction not along the detector rows but along the filter lines.

Alternatively the filter lines according to group II) can be artificially extended by constant continuation of the x-ray image detector in the axial direction followed by hybrid correction along the filter lines or a modified water cylinder correction along the filter lines.

Advantages?

The new methods allow an artifact-free ROI reconstruction within larger body regions such as the abdomen or thorax, which was not possible until now due to the restricted detector surface (in particular with C-arm systems). Moreover the methods can expediently be combined with all FPB algorithms, with which cut off projections cause artifacts. The methods hereby principally aim toward novel approximative and exact FBP algorithms, having non-horizontal filter lines. Methods 1 and 2 are independent of the reconstruction algorithm and can be seen as a preprocessing step before reconstruction. They are therefore generally valid. Methods 3 to 6 are a function of the specific reconstruction algorithm but can however be integrated effectively herein. Moreover the new methods allow an enlargement of the FoV and therefore the reconstruction of larger body regions.

BRIEF DESCRIPTION OF THE DRAWINGS

The invention is described in more detail below with reference to exemplary embodiments illustrated in the drawings, in which:

FIG. 14 shows an original projection and a filter line according to method 3 with associated projection profile, FIG. 15 shows an original projection and filter line according to method 4 with associated projection profile, FIG. 16 shows an original projection and filter line according to method 5 with associated projection profile und FIG. 17 shows an original projection and the original and modified filter line according to method 5 with associated projection profile.

DETAILED DESCRIPTION OF THE INVENTION

Example 1

Method 1 (Group I)

Figure 8:
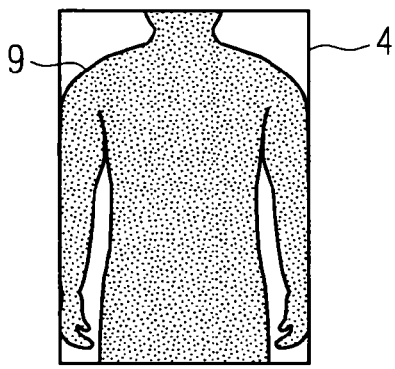
FIG. 8 shows an original projection with axial and transaxial truncation as a basis for explaining method 1.
Figure 9:
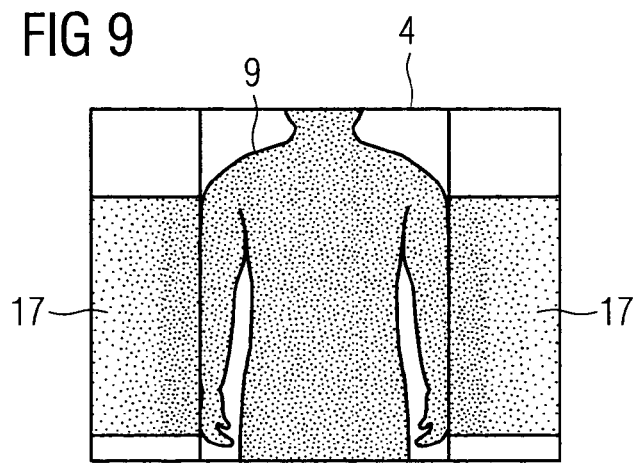
FIG. 9 shows transaxial extension of the x-ray image detector according to FIG. 8 by means of hybrid correction.
Figure 10:
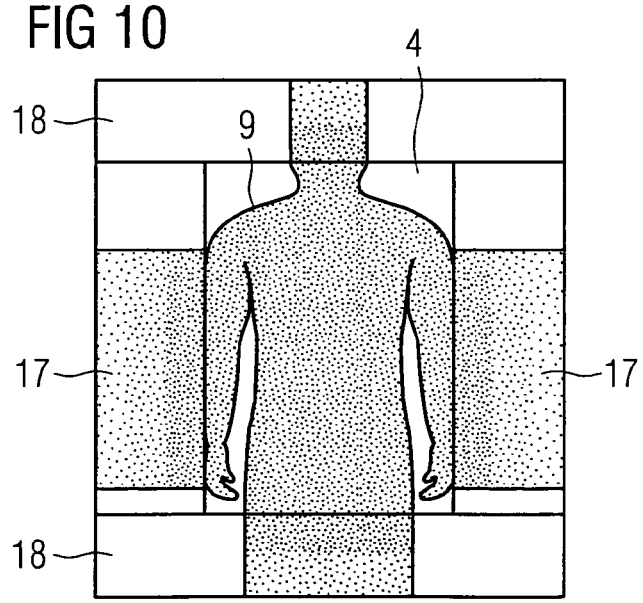
FIG. 10 shows axial extension of the x-ray image detector according to FIG. 9 by means of hybrid correction.

FIG. 8 shows the original projection with axial and transaxial truncation. In FIG. 9 the x-ray image detector 4 has first been extended transaxially with the aid of hybrid correction, so that extension regions with attenuated transaxial continuation 17 result on both sides. In FIG. 10 the x-ray image detector 4 has then been extended axially with the aid of hybrid correction, so that extension regions with attenuated transaxial continuation 18 result on both sides. The size of the extension regions can be configured freely in each instance and can be selected so that it is different for each detector side (left, right, top, bottom). Further flexibility of the method means that steps b) and c) can be interchanged.

Example 2

Figure 11:
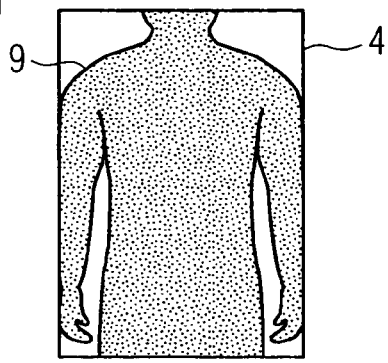
FIG. 11 shows an original projection with axial and transaxial truncation as a basis for explaining method 2.
Figure 12:
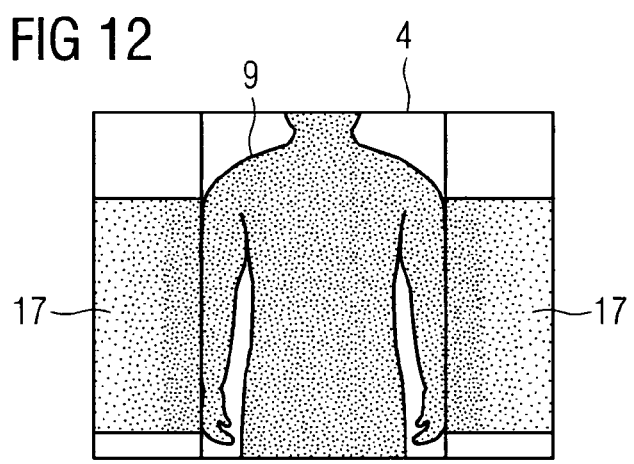
FIG. 12 shows transaxial extension of the x-ray image detectors according to FIG. 11 by means of hybrid correction.
Figure 13:
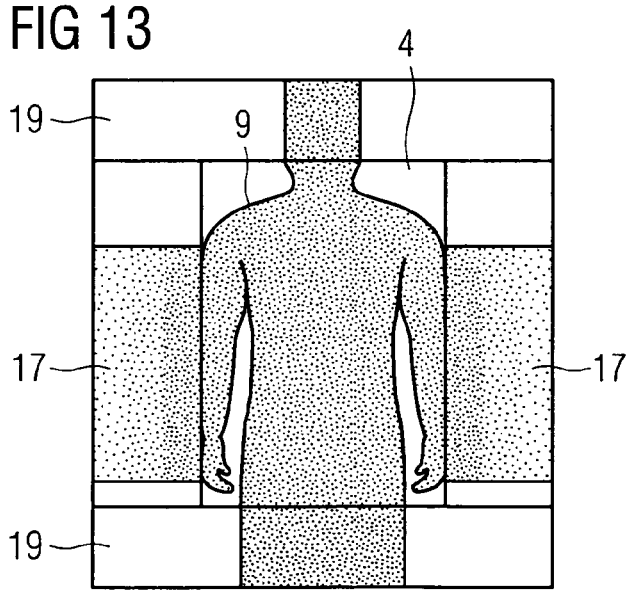
FIG. 13 shows axial extension by means of constant continuation of the x-ray image detector according to FIG. 12 in the axial direction.

Method 2 (Group I) FIGS. 11-13

FIG. 11 shows the original projection with axial and transaxial truncation. In FIG. 12 the x-ray image detector 4 has first been extended with the aid of hybrid correction so that extension regions with attenuated transaxial continuation 17 result on both sides. In FIG. 13 the x-ray image detector 4 has then been extended axially by repeatedly copying and adding the first and last detector rows, so that extension regions with constant axial continuation 19 result on both sides. The size of the extension region can be configured freely in each instance and can be selected so that it is different for each detector side (left, right, top, bottom). The axial extension regions 19 should hereby be set so that no further filter lines are cut off. Further flexibility of the method means that steps b) and c) can be interchanged.

Example 3

Method 3 (Group II) FIG. 14

FIG. 14 shows the original projection and a filter line F3, which is cut off axially on the left and transaxially on the right. Curve 20 shows the corresponding projection profile p(u) for this filter line F3. In the supplemented curve 21 the profile has been continued on both sides by artificially generated projection values 22 by means of hybrid correction. The size of the extension region can be configured freely in each instance and can be selected so that it is different for each side of a filter line F3.

Example 4

Method 4 (Group II) FIG. 15

FIG. 15 shows the original projection, which has already been supplemented by extension regions with constant axial continuation 23 in the axial direction. In the curve 24 the projection profile p(u) of the filter line F3 therefore only shows transaxial truncation. In the supplemented curve 25 the profile has been continued by artificially generated projection values 26 with the aid of hybrid correction. Continuation 27 of the supplemented curve 25 results in the region of constant axial continuation 23. The sizes of the extension regions for the x-ray image detector 4 and filter lines F3 can be freely configured in each instance and can be selected so that they are different for each detector side (top, bottom) and for each side of a filter line F3.

Example 5

Method 5 (Group II). FIG. 16

FIG. 16 shows the original projection together with the projection of a water cylinder 28. In the curve 29 the projection profile p(u) of the filter line F5 only has transaxial truncation in this example. In the supplemented curve 30 the profile of the filter line F5 has been continued by means of artificially generated projection values 31, in that the filter line F5 has been evaluated in this region along the projection of the water cylinder 28. The corresponding projection values are artificially generated by computer-simulated x-ray beams. The center axis (or rotation axis) of the cylinder is oriented parallel to the z-axis of the reference coordinate system. The height of the cylinder is assumed to be infinite, so that only the point of intersection (x, y, 0) of the center axis of the cylinder with the xy-plane and the radius R of the cylinder have to be determined. The three parameters (x, y, R) can be determined in that for example the measured projection values p(u) along the filter line F5 and their first and second derivation in relation to u, p'(u) and/or p"(u) at a point u=u0 are determined. This gives the following equations for calculating (x, y, R):

$$d(u_0,x,y,R) * \mu_w = p(u_0) \quad (1)$$

$$d'(u_0,x,y,R) * \mu_w = p'(u_0) \quad (2)$$

$$d''(u_0,x,y,R) * \mu_w = p''(u_0). \quad (3)$$

Here d refers to the sectional length of the x-ray beam with the water cylinder, d' and d" its first and second derivation in relation to u and $\mu_w$ the attenuation coefficient of water. The procedure should be applied anew for each side of a filter line F5. The modified water cylinder correction differs from the original water cylinder correction in the use of cone-beam geometry. In the original method parallel beam geometry is used to generate the projection values, even though the original projections are acquired using cone-beam geometry.

Example 6

Method 6 (Group III) FIG. 17

FIG. 17 shows the original projection together with the original filter line F3 and the modified filter line F6 shown with a broken line. The curve 32 of the projection profile p(u) of the modified filter line F6 only has transaxial truncation. In the curve 33 the profile has been continued with artificially generated projection values 34 with the aid of hybrid correction. The sizes of the extension regions for the filter lines can be freely configured in each instance and can be selected so that they are different for each side of a filter line. As a further variant it would be possible also to modify the filter line F6 in the transaxial direction before the hybrid correction, for example by continuing this likewise horizontally as soon as it leaves the x-ray image detector 4.

The following method variants result from the inventive embodiment:

Group I, Method 1:
The x-ray image detector 4 is artificially extended transaxially and axially. The extension is based on hybrid correction in each instance (see example 1).

Figure 1:
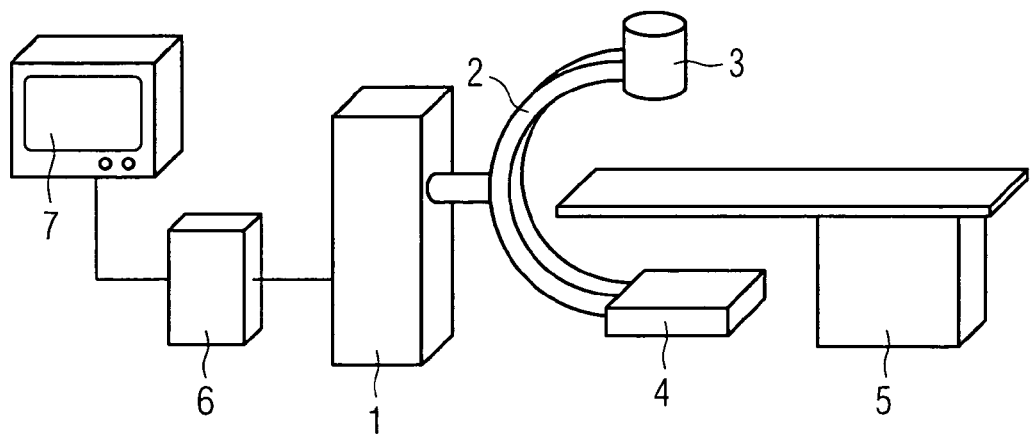
FIG. 1 shows an x-ray diagnostic facility for implementing the method.
Figure 2:
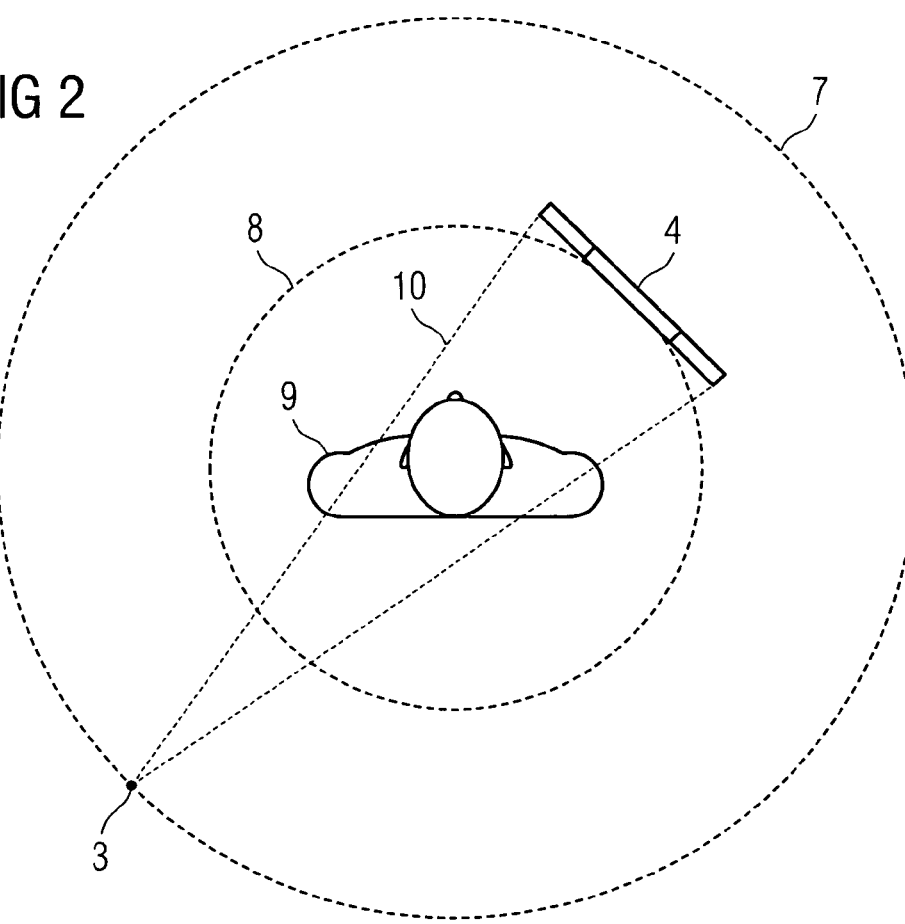
FIG. 2 shows a view of the path of an x-ray image detector and a radiation source around an object to be examined in an axial viewing direction.
Figure 3:
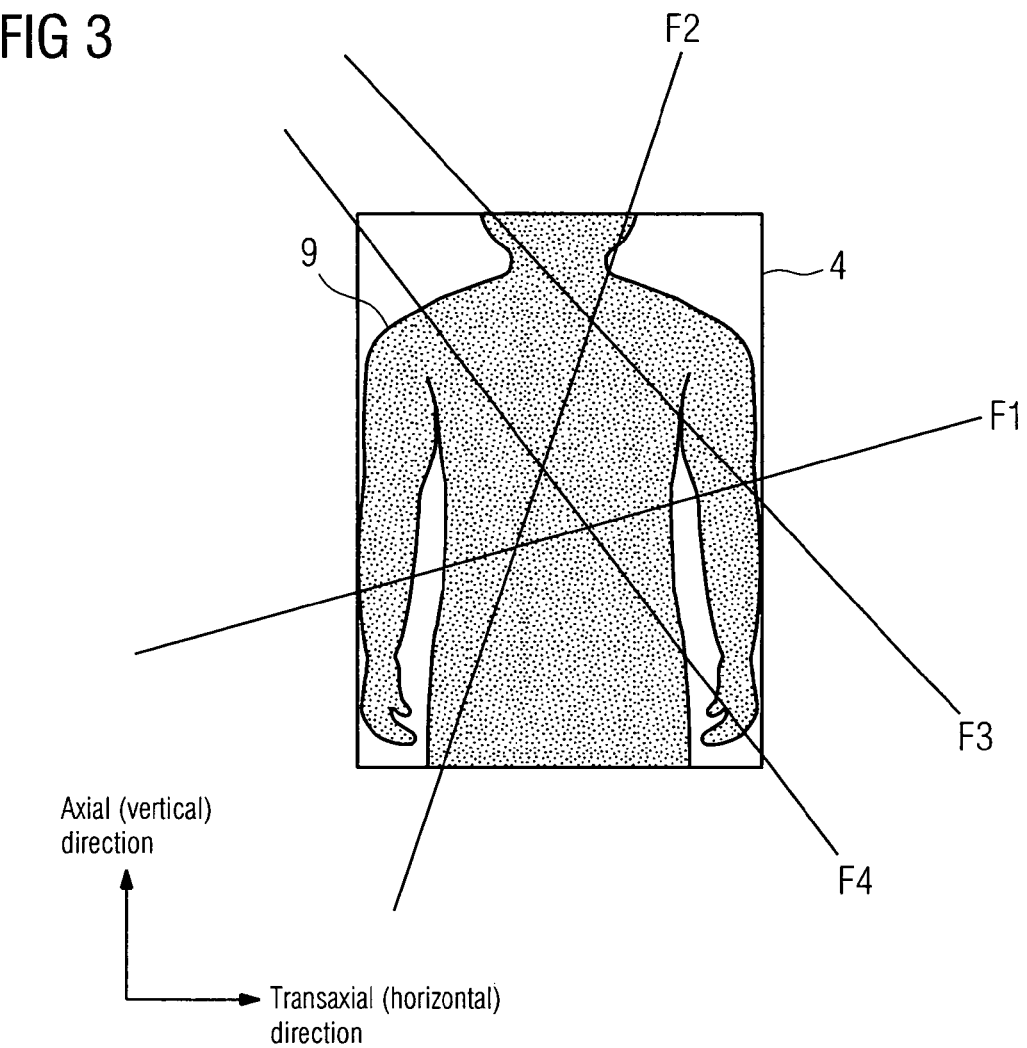
FIG. 3 shows an overview to explain transaxial and axial truncation and possible types of filter line.
Figure 4:
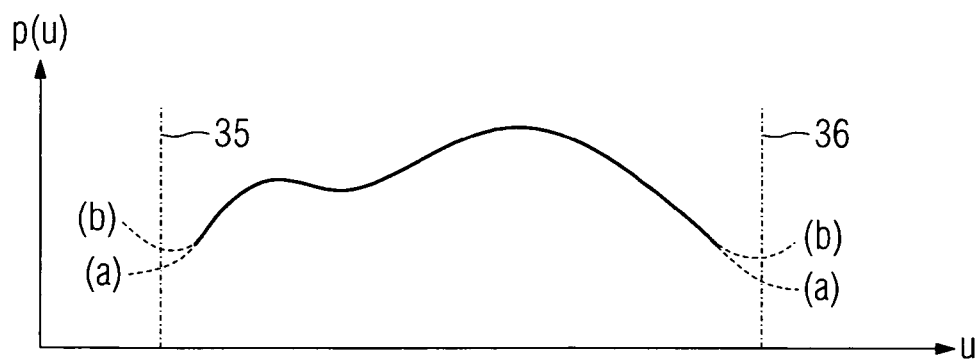
FIG. 4 shows a projection profile p(u) along a cut off detector row.
Figure 5:
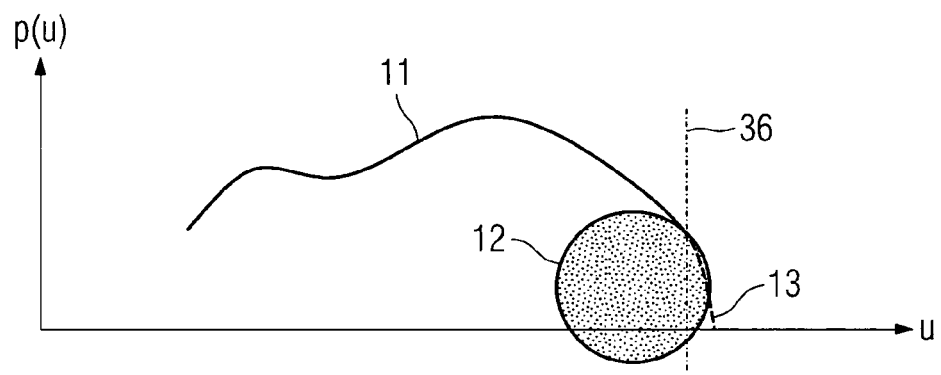
FIG. 5 shows a projection profile p(u) with a water cylinder correction for the right detector edge.
Figure 6:
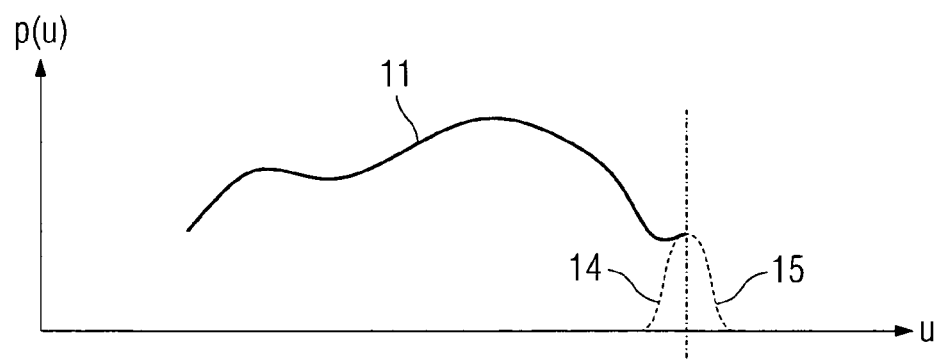
FIG. 6 shows a projection profile p(u) with a Gaussian extrapolation at the right detector edge.
Figure 7:
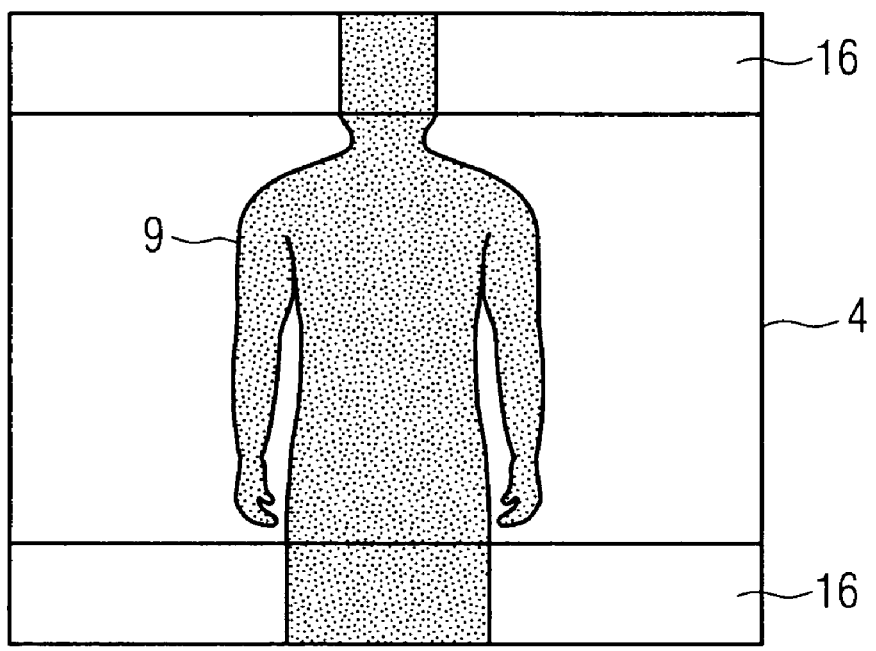
FIG. 7 shows a truncation correction by constant continuation of the x-ray image detector in the axial direction.

Group I, Method 2:
The x-ray image detector 4 is artificially extended transaxially and axially. The transaxial extension is based on hybrid correction. The axial extension happens by means of constant continuation of the x-ray image detector 4 in the axial direction (see also FIG. 5), by repeatedly copying and adding the first and last detector rows (see example 2).

Group II, Method 3:
The filter lines are artificially extended in that the hybrid correction is carried out not along the detector rows as in the original method (see also image 2) but along the filter lines (see example 3).

Group II, Method 4:
The filter lines are artificially extended, by constant continuation of the x-ray image detector 4 in the axial direction (see also FIG. 5) followed by hybrid correction along the filter lines (see example 4).

Group II, Method 5:
The filter lines are artificially extended, by carrying out a modified water cylinder correction along the filter lines (see example 5).

Group III, Method 6:
The filter lines are modified in such a manner that filtering takes place along offset filter lines. These are then artificially extended, by carrying out the hybrid correction along the offset filter lines (see example 6).

The filter part of the filtered backprojection consists of a one-dimensional linear filtering of the detector data. The data can be filtered by means of a convolution operation in real space. Alternatively a convolution operation in real space can be replaced by a multiplication in reciprocal space. With single-row detectors it is clear that the whole detector row is dealt with in one filter step. In the case of multi-row detectors (surface detectors) data has to be found for the one-dimensional filter step. The data to be filtered is collected along one filter line. The data along one filter line can either be convoluted in real space or multiplied in reciprocal space. It should be noted that only the part of real space along a filter line is transformed to reciprocal space with a one-dimensional Fourier transformation. These relationships are basic knowledge in specialist circles, so they have not been explained in the application.

The selection of the filter lines is a function of the reconstruction problem and the reconstruction algorithm used. The frequently applied Feldkamp algorithm described in [1] filters the detector data one-dimensionally row by row, i.e. the filter lines are oriented along the detector rows. In the case of the algorithms for an exact reconstruction of cone-beam data filter lines are generally not arranged along the detector rows, as described for example in [2] to [6].

LITERATURE

[1] L. A. Feldkamp, L. C. Davis, J. W. Kress. "Practical Cone-Beam Algorithm". J. Opt. Soc. Am. A, 1(6): pages 612-619, 1984.

[2] J. Pack, F. Noo, and H. Kudo. "Investigation of saddle trajectories for cardiac ct imaging in cone-beam geometry". Physics in Medicine and Biology, 49(11): pages 2317-2336, 2004.

[3] A. Katsevich. "Image reconstruction for the circle-and-line trajectory". Physics in Medicine and Biology, 49(22): pages 5059-5072, 2004.

[4] A. Katsevich. "Image reconstruction for the circle-and-arc trajectory". Physics in Medicine and Biology, 50(10): pages 2249-2265, 2005.

[5] B. E. Nett, T. Zhuang, and G.-H. Chen. "A cone-beam fbp reconstruction algorithm for short-scan and super-short-scan source trajectories". In Fully 3D Image Reconstruction in Radiology and Nuclear Medicine, Salt Lake City, Utah, USA, Jul. 6-Jul. 9, 2005.

[6] J. Pack and F. Noo. Cone-beam reconstruction using 1D filtering along the projection of m-lines. Inverse Problems, 21(3): pages 1105-1120, 2005.

[7] J. Hsieh, E. Chao, J. Thibault, B. Grekowicz, A. Horst, S. McOlash, and T. J. Myers. A novel reconstruction algorithm to extend the CT scan field-of-view. Medical Physics, 31(9): pages 2385-2391, 2004

[8] M. Zellerhoff, B. Scholz, E.-P. Rührnschopf and T. Brunner. Low contrast 3D-reconstruction from C-arm data. SPIE Medical Imaging 2005, 5745: pages 1605-7422, 2005

[9] Bernhard Scholz, Fächerstrahlbasierte Wasserzylinderextrapolation von abgeschnittenen Projektionen zur Behandlung von Trunkierungsartefacten (Fan-beam based water cylinder extrapolation from cut-off projections for dealing with truncation artifacts), former patent application DE 10 2006 014 629.8 dated 29.03.2006.

[10] T. Flohr, K. Stierstorfer, H. Bruder, J. Simon, A. Polacin, and S. Schaller. Image reconstruction and image quality evaluation for a 16-slice CT scanner. Medical Physics, 30(5): pages 832-845, 2003

[11] M. Kachelrieβ, M. Knaup, and W. A. Kalender. Extended parallel backprojection for standard three-dimensional and phase-correlated four-dimensional axial and spiral cone-beam CT with arbitrary pitch, arbitrary cone-angle, and 100% dose usage. Medical Physics, 31(6): pages 1623-1641, 2004

[12] Magnusson et al., "Handling of Long Objects in Iterative Improvement of Nonexact Reconstruction in Helical Cone-Beam CT", IEEE Trans. Med. Imaging Vol. 25, NO. 7, July 2006, pages 935-940

The invention claimed is:

1. A method for correcting a truncation artifact in a reconstruction for a projection image of a computed tomography, comprising:
    emitting divergent radiation by a radiation source;
    transilluminating an object to be examined by the divergent radiation in different projection directions;
    detecting the divergent radiation penetrating the object by an x-ray image detector for generating projection data;
    performing a filtered backprojection by filtering the projection data along a non-horizontal filter line in the x-ray image detector;
    extending the non-horizontal filter line by transaxially and axially artificially extending the x-ray image detector; and
    correcting the truncation artifact based on the extension.

2. The method as claimed in claim 1, wherein the truncation artifact is corrected regardless of a specific location and orientation of the non-horizontal filter line.

3. The method as claimed in claim 2, wherein the x-ray detector is transaxially and axially artificially extended based on a hybrid correction comprising a water cylinder correction and a Gaussian extrapolation.

4. The method as claimed in claim 2, wherein the x-ray detector is transaxially artificially extended based on a hybrid correction comprising a water cylinder correction and a Gaussian extrapolation and axially artificially extended based on a constant continuation of the x-ray image detector in an axial direction.

5. The method as claimed in claim 1, wherein the truncation artifact is corrected as a function of a specific position and orientation of the non-horizontal filter line with the non-horizontal filter line being retained.

6. The method as claimed in claim 5, wherein the non-horizontal filter line is artificially extended by a hybrid correction comprising a water cylinder correction and a Gaussian extrapolation along the non-horizontal filter line.

7. The method as claimed in claim 6, wherein the non-horizontal filter line is artificially extended by a constant continuation of the x-ray image detector in an axial direction followed by the hybrid correction comprising the water cylinder correction and the Gaussian extrapolation along the non-horizontal filter line.

8. The method as claimed in claim 6, wherein the non-horizontal filter line is artificially extended by a modified water cylinder correction along the non-horizontal filter line.

9. The method as claimed in claim 1, wherein the truncation artifact is corrected by introducing a new modified non-horizontal filter line with the filtering taking place along an offset artificially extended non-horizontal filter line.

10. The method as claimed in claim 9, wherein the new modified non-horizontal filter line is artificially extended by a hybrid correction comprising a water cylinder correction and a Gaussian extrapolation along the offset artificially extended non-horizontal filter line.

11. The method as claimed in claim 1, wherein the projection image is recorded by the x-ray detector and extended by determining an attenuation of the divergent radiation outside the projection image.

12. The method as claimed in claim 1, wherein the non-horizontal filter line is predefined.

13. An x-ray image device, comprising:
    an x-ray source that emits divergent radiation;
    an x-ray image detector that detects the divergent radiation penetrating an object to be examined for generating projection data; and
    a computer that:
        performs a filtered backprojection by filtering the projection data along a non-horizontal filter line in the x-ray image detector, and
        corrects a truncation artifact in the filtered backprojection by extending the non-horizontal filter line via transaxially and axial artificially extending the x-ray image detector.

* * * * *